(12) United States Patent
Malmgren et al.

(10) Patent No.: US 6,846,924 B1
(45) Date of Patent: Jan. 25, 2005

(54) METHOD OF PRODUCING AN ABSORBENT MATERIAL, AN ABSORBENT MATERIAL AND ABSORBENT ARTICLES INCLUDING THE MATERIAL IN QUESTION

(75) Inventors: Kent Malmgren, Sundsvall (SE); Bengt Widberg, Sundsvall (SE)

(73) Assignee: SCA Hygiene Products AB (SE)

( * ) Notice: Subject to any disclaimer, the term of this patent is extended or adjusted under 35 U.S.C. 154(b) by 0 days.

(21) Appl. No.: 09/101,341

(22) PCT Filed: Dec. 18, 1996

(86) PCT No.: PCT/SR96/01698

§ 371 (c)(1),
(2), (4) Date: Jul. 8, 1998

(87) PCT Pub. No.: WO97/25463

PCT Pub. Date: Jul. 17, 1997

(30) Foreign Application Priority Data

Jan. 10, 1996 (SE) .................................... 9600087

(51) Int. Cl.[7] ............................ C07H 1/00; C08B 37/04; C08B 37/08; C08B 11/00; C08B 35/00

(52) U.S. Cl. ........................... 536/124; 536/3; 536/20; 536/56; 536/98; 536/102; 536/114

(58) Field of Search ................. 536/3, 20, 56, 536/98, 102, 114, 124

(56) References Cited

U.S. PATENT DOCUMENTS 4,197,371 A * 4/1980 Holst et al. .................... 521/84
4,250,306 A * 2/1981 Lask et al. ..................... 536/88
4,257,903 A * 3/1981 Kucera et al. ............... 536/114
5,532,221 A * 7/1996 Huang et al. .................. 514/53
5,532,350 A * 7/1996 Cottrell et al. ................ 536/76
5,549,861 A * 8/1996 Huber et al. ................ 264/187
5,550,189 A * 8/1996 Qin et al. .................... 536/124
5,601,771 A * 2/1997 Ruf ............................. 264/187

FOREIGN PATENT DOCUMENTS

| EP | 232121 | * | 8/1987 |
| EP | 410323 A | * | 1/1991 |
| FR | 0 668 078 A2 | | 8/1995 |
| JP | 401148874 A | * | 6/1989 |
| WO | WO 93/12275 | | 6/1993 |
| WO | WO97/25463 | | 7/1997 |

OTHER PUBLICATIONS

"Absorbency"; by P.K. Chatterjee; pp. 232–234; 1985.

* cited by examiner

Primary Examiner—James O. Wilson
Assistant Examiner—Everett White
(74) Attorney, Agent, or Firm—Burns, Doane, Swecker & Mathis, L.L.P.

(57) ABSTRACT

The present invention relates to a method of producing polysaccharide fibres (8), wherein the polysaccharide is dissolved and the solution is sprayed into a bath (7) which contains a water-miscible organic solvent and a cross-linker. The invention also relates to a polysaccharide fibre (8) produced by the method, and to an absorbent article which includes the polysaccharide fibre (8).

13 Claims, 5 Drawing Sheets

METHOD OF PRODUCING AN ABSORBENT MATERIAL, AN ABSORBENT MATERIAL AND ABSORBENT ARTICLES INCLUDING THE MATERIAL IN QUESTION

TECHNICAL FIELD

The present invention relates to a method of producing polysaccharide fibre, the polysaccharide fibre thus produced and an absorbent article which includes polysaccharide fibres.

BACKGROUND OF THE INVENTION

Superabsorbents, that is to say absorbent material which is capable of absorbing several times, normally more than ten times, its own weight of water or body fluid, is used in absorbent articles, such as diapers, incontinence guards sanitary napkins, to enhance the absorbency of the absorbent body of the article and also retention capacity, the remainder of the absorbent body normally consisting of cellulose fibres so-called fluff pulp.

Polyacrylic acid is the polymer most used as superabsorbent non-renewable base. Polyacrylic acid is produced from oil. Since crude oil is a natural resource that is non-renewable, the use of oil as a starting material in the manufacture of polyacrylic acid creates a problem from an environmental aspect.

With the intention of resolving this problem, endeavors have been made to produce superabsorbents on the basis of renewable primary materials. These primary materials have included the different polysaccharides, such as starch and cellulose. One polymer that has been used to a great extend in this context is carboxymethyl cellulose. This is a cellulose derivative with carboxymethyl as a subsistent. The properties of the polymer are contingent on the degree of polymerization, DP, and the degree of substitution, DS. Carboxymethyl cellulose is relatively cheap and hu high affinity to water-based liquids.

However, the admixture of carboxymethyl cellulose in absorbent articles such as diapers, incontinence guards and sanitary napkins is associated with serious drawbacks. When the article is wetted tiring use, the carboxymethyl cellulose will dissolve and therewith increase the viscosity of the liquid discharged by the wearer. This dramatically reduces the liquid dispersion rate. So-called gel blocking occurs. Carboxymethyl cellulose that has a degree of substitution below 0.35 is not soluble in water and could therefore be used favorably in absorbent articles with regard to the aspect of gel blocking. However, carboxymethyl cellulose that has a degree of substitution below 0.35 has pour absorption properties in comparison with polyacrylates. In other words, the carboxymethyl cellulose must have a degree of substitution greater than 0.35 in order to hive good absorption properties, although such carboxymethyl cellulose is soluble in water and therewith presents a gel blocking problem.

Another drawback with the superabsorbents that are commercially available at present is the administration foam. The superabsorbent is normally added to the article in which it shall be included in the form of grains, flakes or granules. A special metering apparatus is required to add superabsorbent in this form, and it is difficult to obtain uniform distribution on of superabsorbent in the fibrous pulp body.

Superabsorbent in fibre form would be easier to meter. Because the absorbent body into which the superabsorbent is to be administered normally consists of fibres, there is a danger of superabsorbent particles separating-out from the fibre matrix. This problem is alleviated with superabsorbents in fibre form. Although polyacrylate fibres are commercially available, they have not been used to any great extent. This is probably due to their high price and poor swellability.

A number of attempts have been made to produce polysaccharide fibres for use in sanitary products. WO 93/12275 discloses solvent spinning of polysaccharide fibre. However, the swelling properties of polysaccharide fires produced in accordance with known techniques is too poor for such fibres to be of interest as a substitute for conventional superabsorbent material.

OBJECT OF THE INVENTION

An object of the present invention is to provide a superabsorbent material which is based on renewable primary material and which has an acceptable performance capacity in comparison with conventional superabsorbent materials.

Another object of the invention is to produce a superabsorbent material in an administration form which facilitates uniform metering of the superabsorbent material to a pulp body.

SUMMARY OF THE INVENTION

A method for producing a polysaccharide fibre of the kind mentioned in the introduction and having properties which enable the aforesaid problems associated with conventional superabsorbent material to be avoided is characterized in accordance with the invention by dissolving the polysaccharide in a solvent, extruding the solution down into a bath which includes a water-miscible organic solvent, preferably an alcohol, such as methanol, ethanol, or isopropanol, or a ketone such as acetone, and a cross-linking agent, such as a polyelectrolyte or a metal salt preferably a salt of a divalent, trivalent or quadrivalent ion, such as calcium, magnesium, iron, aluminium or zirconium

DESCRIPTION OF THE INVENTION

Figure 1:
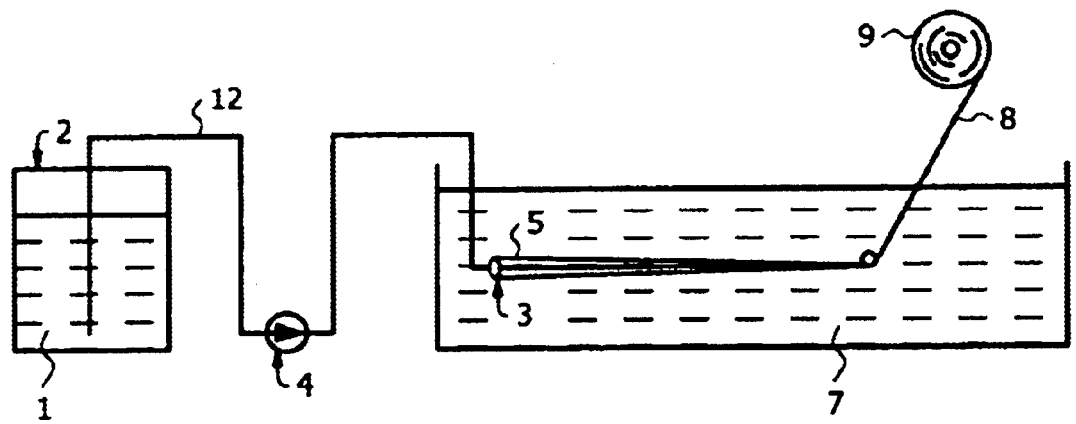
FIG. 1 shows an exemplary system for producing polysaccharide fibers.

Those polysaccharides that can be used to produce a polysaccharide fibre in accordance with the invention are, for instance, carboxymethyl cellulose, starch, cellulose xanthane, gelan, chitin, chitosan, guar gum, alginate.

As before mentioned, carboxymethyl cellulose, which is a cellulose derivative, is particularly well-suited for this purpose. The properties of the polymer are contingent on the degree of polymerization, DP, and the degree of substitution, DS.

The degree of polymerization, DP, denotes the number of monomer units in the polymer chain that influence the viscosity of an aqueous solution of the polymer.

The degree of substitution, DS, denotes the mean member of carboxymethyl substituents in the polymer chain. The degree of substitution influences the swelling properties of the polymer, and a degree of substitution above 0.35 gives a water-soluble polymer.

As before mentioned, a degree of substitution above 0.35 is desirable in order to obtain a high absorbency. However, this would result in a water-soluble polymer and therewith create gel-blocking problems.

Consequently, it would be desirable to produce a polysaccharide, for example, a carboxymethyl cellulose, that had a degree of substitution greater than 0.35 and which did not dissolve in water. This object is realized in accordance with the invention, by cross-linking the polymer. This cross-linking may be covalent or ionic.

The use of conventional crosslinkers to cross-link the polymer, such as epichlorhydrin and formaldehyde, would cause the coagulate to precipitate very slowly and fasten to the extrusion nozzle, therewith creating serious disturbances in a large-scale process.

According to the invention, the polymer is ionically cross-linked with the aid of polyelectrolytes or polyvalent metal ions, especially calcium, zirconium, aluminum or iron(III). When carboxymethyl cellulose it to be cross linked, it is probable that cross-linking is effected by the formation of bonds between the carboxyl groups. Cross-linkers in the form of salts give fibres that are easily spun. The salt in which the polyvalent metal ion or the polyelectrolyte is present shall be soluble in water. The counter-ion to the metal ion or the polyelectrolyte, in other words the anion, is selected accordingly. Chloride is a suitable anion in this respect.

The cross-linked superabsorbent is then distributed in an absorbent body, which is normally comprised of cellulose pulp. The pulp may be in reels, bales or sheets winch are dry-defibrated and converted into a fluffed state to form a pulp mat. As before mentioned, the material in the absorbent body may be cellulose fibres. Examples of other fibres conceivable in this regard are cotton fibres and synthetic fibres. It is also known to use foamed material in the absorbent body.

The problem of administering a superabsorbent in grain, flake of granule form evenly in the absorbent body is solved in accordance with the invention by choosing another administering form, namely a fibre form.

These fibres are produced in accordance with the invention by solvent spinning. Solvent spinning is carried out by pumping a polymer solution to a spinning nozzle, and extruding the solution into a bath containing a water-miscible organic solvent, such as an alcohol. This solvent causes the polymer to precipitate in the form of fibres.

The extrusion bath may also contain water. The volume of water in the extrusion bath is determined by the fact that a given lowest organic solvent content is required to obtain good quality fibers. The lowest organic solvent content is about 70 vol %. The extrusion bath may thus contain about 0–30 vol % water.

As the polysaccharide which was earlier dissolved in water precipitates in the extrusion bath, the bath will become enriched with water. For the above-said reason, this water must be removed contiguously to prevent the organic solvent content falling beneath about 70 vol %. The extrusion bath also includes one or more cross-liking agents in addition to the organic solvent. This method results in the simultaneous forming of fibres and cross-linking of the polymer.

The fibres are reeled-up from the extension bath, and dried and cut into appropriate lengths. An appropriate fibre length is 2–20 nm, preferably 48 mm. After this has been done, the fibres can be admixed in absorbent bodies intended for use in absorbent articles, such as diapers, incontinence guards and sanitary napkins.

According to one alternative a nt of the invention, the fibres may also be subjected to post-treatment, in which the fibres are cross-linked covalently. Surprisingly, this covalent cross-linking of the fibres has been found to greatly increase the capillary liquid-retaining capacity of the fibres.

The following explanation as to why the covalent cross-linking enhances the liquid-retaining capacity of the fibres shall be seen solely as an hypothesis of how the invention can be assumed to function. The described hypothesis, or theory, shall not be considered as limiting the scope of the invention, but shall be seen solely as a conceivable model of the manner in which the invention works, with the intention of facilitating an understanding of the invention.

The reason why the covalently bonded fibre have a surprisingly good retention ability may be because the covalent cross-linked fibres swell rapidly and copiously. The risk of gel-blocking decreases; a fibre network containing the covalently cross-linked fibres has very large pores in a swollen state. The fibres expand quickly and copiously, particularly longitudinally, which favours the expansion cm the network in which the covalently cross-linked fibres are mixed and thereby enhances dispersion of liquid, or fluid, in the network.

This covalent surface cross-linking of the fibres can be achieved with various conventional cross-linkers, for example: 2,4,6-trichloro-1,3,5-triazine epichlorohydrin, bis (epoxypropyl) ether, dichloroethane, divinylsulfone, ethylene glycol-bis(epoxypropyl) ether, formaldehyde, vinyl cyclohexane dioxide, 1,3-dichloro-2-propanol, 1,3-bis(β-hydroxy-t,-chloropropoxy)-2-propanol, 1,3-bis (β-hydroxy-t,-chloropropoxy) ethane, 1,2:3,4-diepoxybutane, 1,1:5,6-diepoxyhexane, 2,3-dibromo-1-propanol, 2,3-dichloro-1-propanol, 2,2-dichloroethyl ether, methyl bis(acrylamide), N,N'-dimethylol(methylbis(acrylamide)), trisacrylol hexahydro-triazin, acrylamidemethyl chloroacetamide, 2,4, 6-trichloropyrimidine, 2,4,5,6-tetrachloropyrimidine, cyanuric chloride, triallyl cyanurate, dichloroacetic acid, phosphorus oxychloride, bis(acrylamido) acetic acid.

These cross-linkers and cross-lining methods using these cross-linkers are described by Dean, Ferguson and Holst in the book "Absorbency", edited by P. K. Chatterjee, Elsevier Science Publishing Company, 1985.

In accordance with the invention, polysaccharide fibres may be produced by moulding (casing) as an alternative to extrusion. The polysaccharide fibres are sprayed into a bath which contains solvent and or more cross-linkers as described above, both when extruding and casting the fibres. However, when casting the fibres the solution is not sprayed through a nozzle as in the case with extrusion, but is instead sprayed onto a plate rotating in the bath.

The polysaccharide fibres produced in accordance with the invention can now be used as conventional superabsorbents, in other words can be mixed with fluff pulp or applied in layers between fluff pulp or between tissue layers. They can also be combed with other superabsorbents.

It will be understood that the invention is not restricted to the combinations described here, but that all combinations of solvents, cross-linked and polysaccharides are included in the inventive concept
Embodiments

EXAMPLE 1

Spinning of CMC-Fibres Having Different Aluminum Contents

Equipment

Rayon spinning laboratory equipment was used, this equipment being shown in FIG. 1.

Figure 2:
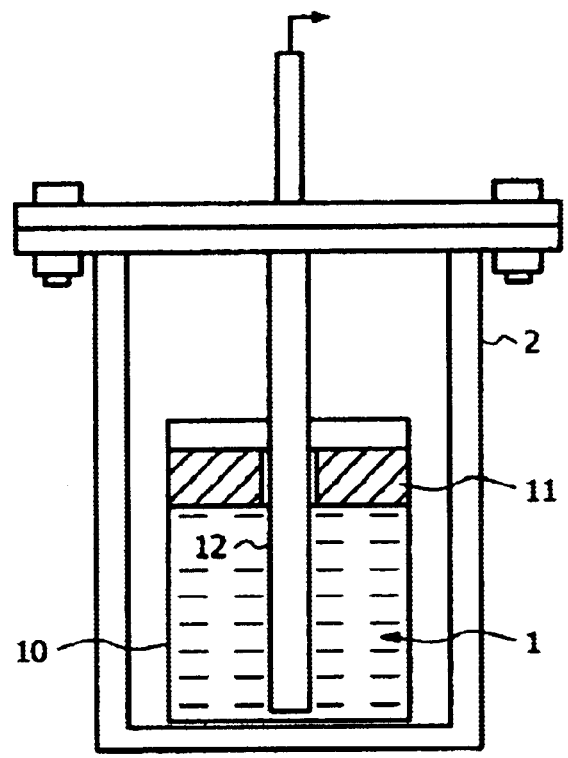
FIG. 2 shows a pressure chamber of an exemplary system for producing polysaccharide fibers.

The equipment comprised
A pressure chamber, shown in detail in FIG. 2.
A gear pump.
A spinning nozzle.
A rectangular plexiglass tank measuring 890×195×190 mm, to be used as an extrusion bath.

A beaker 10 containing a de-aerated carboxymethyl cellulose (CMC) solution 1 was placed in a pressure chamber 2. A lead weight 11 was placed on top of the solution. The chamber 2 was sealed and air having a pressure of 7.5 bars forced the CMC solution through a steel 12 and via a gear pump 4 to the spinning nozzle 3. The lead weight 11 prevented air from entering between the CMC-solution 1 and the steel pipe 12. The spinning nozzle 3 contained 20 holes 5, each having a diameter of 200 $\mu$m.

The CMC-solution 1 was extruded out into the extrusion bath 7 through the spinning nozzle 3. The extrusion bath 7 contained ethanol and aluminium chloride.

CMC-fibres 8 were drawn through the extrusion bath with the aid of a variable speed roller 9 driven by an electric motor. The CMC-fibres were held beneath the surface of the extrusion bath with the aid of a glass rod.

The fibres were then washed in ethanol (95%), being held for two minutes in the alcohol. This procedure was reed two times. The washed fibres were dried at room temperature and then cut into lengths of 6 mm.

A Method of Preparing the Carboxymethyl Cellulose Solution

Different concentration a of CMC were tested: 8% Cekol 10000 and 7% Cekol 5000 from Metsä-Särla Oy. Cekol 10000 and Cekol 50000 had mutually the same DS (0.6–0.9) but Cekol 50000 had a higher DP than Cekol 10000.

CMC in granule or powder form was mixed with water. The mixture was stirred (agitated) manually and the mixture then allowed to stand in a closed container for at least two calendar days.

Figure 3:
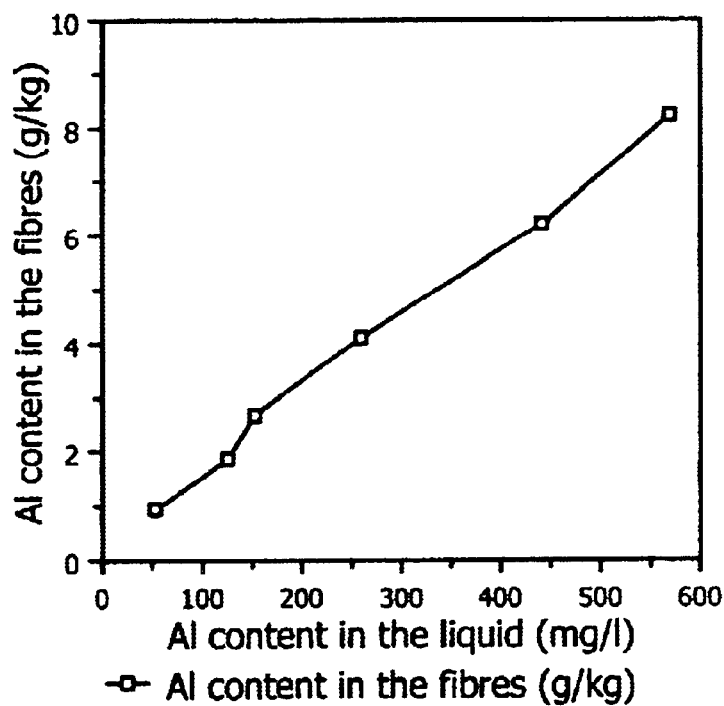
FIG. 3 is a graph showing Al content in the liquid vs. Al content in the fibers, for an exemplary embodiment in which Cekol 10000 was used as the starting material.
Figure 4:
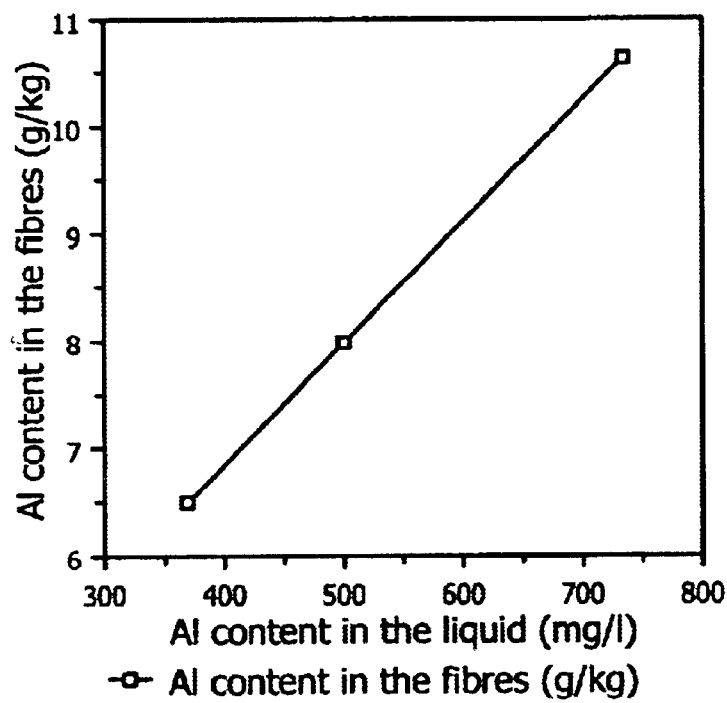
FIG. 4 is a graph showing Al content in the liquid vs. Al content in the fibers, for an exemplary embodiment in which Cekol 50000 used as the starting material

The mixture was centrifuged and evacuated alternatively, until all air bubbles in the mixture had disappeared. 600 g of the CMC-solution were placed in a plastic beaker (800 ml), the breaker being subjected to a vacuum for thirty minutes in order to remove air bubbles from the solution.
The Extension Bath The extension bath had a volume of 8l. Originally, it consisted of 95 vol % ethanol and 5 vol % water. Aluminium chloride was then added to the bath. The amount of aluminum chloride in the bath varied as shown in FIGS. 3 and 4. The concentration of aluminium chloride fell during the process, as the fibres absorbed the salt. It was therefore necessary to add aluminum chloride during the spinning process. The concentration of aluminium chloride was never allowed to fall by more than 10% during the process.
The aluminum Content of the Fibres CMC-fibres were produced with different aluminum contents, by varying the aluminum content of the extrusion bath. FIG. 3 shows the result obtained when using Cekol 10000 as the starting material, while FIG. 4 shows the result obtained when using Cekol 50000 as the starting material.

EXAMPLE 2

Producing CMC-Fibres with Different Baths

With the intention of discovering whether or not fibres could be formed in extrusion baths of mutually different compositions, tests were carried out with aluminium salts, iron salts, zirconium salts and magnesium salts in a bath with different solvents. The CMC used was Cekol 50000. The solvents tested were ethanol, methanol, isopropanol and acetone. The following bath compositions were tested:

| Metal salt | Liquid salt |
| --- | --- |
| 1. 4.4 g AlCl$_3$—6H$_2$O/liter solution | 95 vol-% ethanol + 5 vol-% water |
| 2. 4.4 g AlCl$_3$—6H$_2$O/liter solution | 95 vol-% methanol + 5 vol-% water |
| 3. 4.4 g AlCl$_3$—6H$_2$O/liter solution | 85 vol-% acetone + 15 vol-% water |
| 4. 4.4 g AlCl$_3$—6H$_2$O/liter solution | 95 vol-% isopropanol + 5 vol-% water |
| 5. 5.3 g FeCl$_3$—6H$_2$O/liter solution | 95 vol-% ethanol + 5 vol-% water |
| 6. 5.3 g FeCl$_3$—6H$_2$O/liter solution | 95 vol-% methanol + 5 vol-% water |
| 7. 5.3 g FeCl$_3$—6H$_2$O/liter solution | 95 vol-% acetone + 5 vol-% water |
| 8. 5.3 g FeCl$_3$—6H$_2$O/liter solution | 95 vol-% acetone + 5 vol-% water |
| 9. 6.0 g ZrCl$_4$/liter solution | 95 vol-% ethanol + 5 vol-% water |
| 10. 6.0 g ZrCl$_4$/liter solution | 95 vol-% methanol + 5 vol-% water |
| 11. 6.0 g ZrCl$_4$/liter solution | 95 vol-% isopropanol + 5 vol-% water |
| 12. 15.5 g MgCl$_2$—6H$_2$O/liter solution | 95 vol-% ethanol + 5 vol-% water |
| 13. 15.5 g MgCl$_2$—6H$_2$O/liter solution | 95 vol-% methanol + 5 vol-% water |
| 14. 15.5 g MgCl$_2$—6H$_2$O/liter solution | 78 vol-% acetone + 22 vol-% water |
| 15. 15.5 g MgCl$_2$—6H$_2$O/liter solution | 90 vol-% isopropanol + 10 vol-% water |

Results

Fibres were obtained with all extrusion bath compositions.

EXAMPLE 3

Polyelelectrolytes as Cross-Linkers

CMC-fibres we produced from Cekol 50000 in accordance with the invention, there being used a spinning bath containing polyelectrolytes dissolved in 80 vol % ethanol and 20 vol % water. The compositons of the different spinning are described below.

| Polyelectrolyte | Trade name | Content (weight %) |
| --- | --- | --- |
| Polyvinyl amine | Basocoll (BASF) | 0.05 |
| Polybrene (quaternary polyamine) | Polybrene (Aldrich) | 0.1 |

Result

Fibres could be produced in both baths.

EXAMPLE 4

Producing Fibres From Different Types of Polysaccharides

Concentrated aqueous solutions were produced from the following polysaccharides.

| Polysaccharide | Trade name (manufacturer) | Concentration (weight %) |
|---|---|---|
| CMC | Cekol 2000 (Metsä-Serla OY) | 12 |
| CMC | Cekol 4000 (Metsä-Serla OY) | 10 |
| CMC | Cekol 10000 (Metsä-Serla OY) | 8 |
| CMC | Cekol 30000 (Metsä-Serla OY) | 7.5 |
| CMC | Cekol 50000 (Metsä-Serla OY) | 7 |
| Guar gum | Meypro ® Guar (Meyhall) | 10 |
| Bean gum | Meypro ® LBG (Meyhall) | 10 |
| Pectin | Genu ® pectin type X-0905 (Copenhagen Pectin) | 5 |

The solutions were then used to produce fibres in accordance with the invention, in a spinning bath consisting of 8 g $AlCl_3$ $6H_2O$/1 in 95 vol % ethanol and 5 vol % water.

Results

Fibres could be produced from all of these polysaccharides.

EXAMPLE 5

Covalent Cross-Bonding of Spun CMC-Fibres

CMC-fibres produced from Cekol 50000 in accordance with Example 1 by spinning in a bath consisting 3 g $AlCl_3$ $6H_2O$/1 in 95 vol % and 5 vol % water were used in this test 5 g of fibres cut to a length of 6 mm were placed in a glass beaker containing 250 ml of distilled er and allowed to swell for about one minute. 250 ml of a 2 percent by weight solution of 2,4,6-trichloro-1,3.5-triazin in acetone were then added to the beaker.

After stirring the bath gently for five minutes, a 2.5 M NaOH-solution was added drop-wise while continuing to stir the bath. A total of 30 ml NaOH-solution were added over a period of fifteen minutes. The bath was then stirred gently for a further thirty minutes, whereafter the liquid was removed and the fibres were washed repeatedly with 95 vol % ethanol. The fibres were then dried at room temperature.

EXAMPLE 6

Characterization of Absorption Properties with the Aid of Liquid Porosymmetry

Liquid Porosymmetry

A fibre network ad of fibres produced in accordance with the invention was characterized with the aid of a PVD-apparatus (Pore Volume Distribution) manufactured by Textile Research Institute, Princeton, U.S.A. The function of the PVD-apparatus is described concisely in miller, B and Tyomkin, L., Text. Res. J. 56 (1986) 35 and described briefly below, referring to FIG. 9.

Liquid was applied to the sample (in this case 0.9% NaCL-solution and so-called synthetic urine, respectively) in an excess amount and the sample allowed to absorb the liquid over a given period (in this case 5 h). The sample 13 was then placed in a chamber 14 on a membrane 15, and a porous plate 16, a mechanical load (in this case 2.5 kPa) in the form of a lead weight being placed on top. The chamber was then sealed-off and the chamber air pressure increased progressively in stages with the aid of a computer-controlled pressurizing system, the liquid being exited from the sample through a small-pore membrane (in this case a pore size of 0.22 μm). The weight of the liquid pressed from the sample was recorded by a balance scale 17.

According to Laplace equation [1], a given pressure corresponds to a pore radius.

$$\Delta P = \frac{2\gamma Cos\theta}{x} \quad [1]$$

where

ΔP= The pressure necessary for pressing-out liquid hydraulically.

γ= The surface tension of the liquid.

θ= Contact age between liquid and material.

r= Pore radius.

Figure 7:
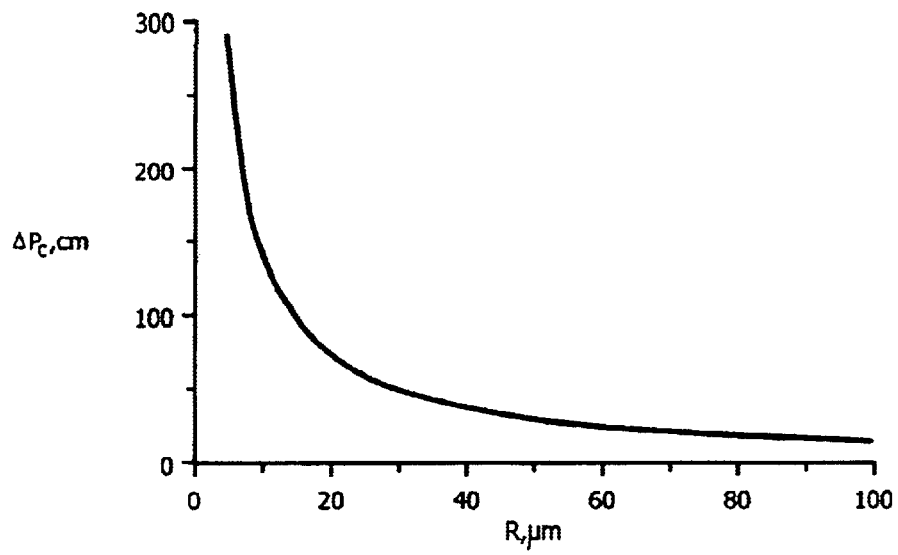
FIG. 7 is a graph showing pore radius vs. pressure difference, according to an exemplary aspect.

When surface tension and contact angle are constant the pressure increase is thus reciprocally proportional to the pore radius This gives a relationship between pressure difference and liquid volume, which can be described schematically in accordance with the FIG. 7 diagram.

Figure 8:
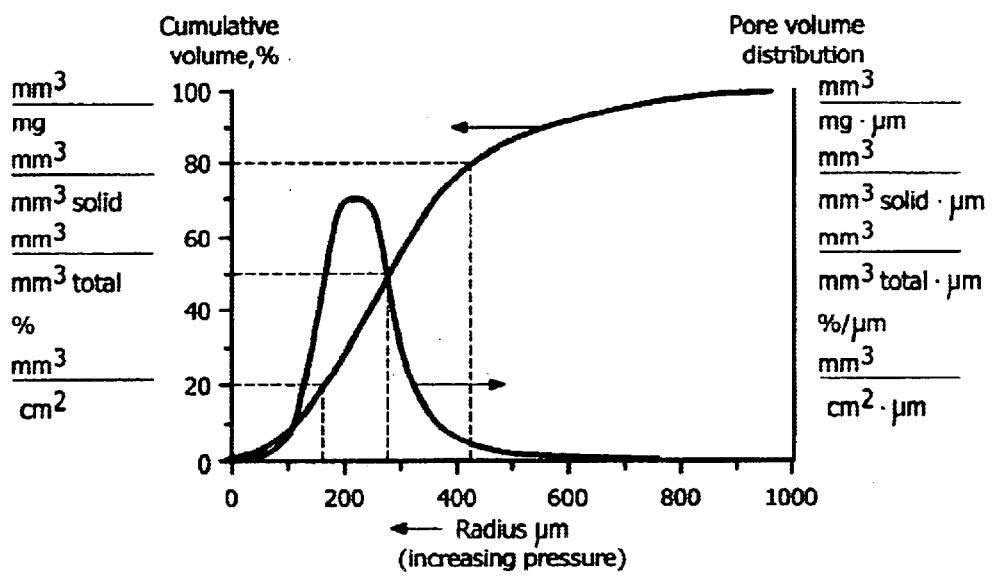
FIG. 8 is a graph showing an exemplary pore volume distribution.

When this cumulative relationship is deviated them is obtained a pore vole distribution as shown diagrammatically in FIG. 8. The distribution function reveals the amount of liquid retained by pores of a given size.

In this work, liquid contained in pores greater than 3 mm has been defined as capillary liquid, and liquid in pores smaller than 3 mm as gel liquid. The capillary liquid is found in pores between the fibres, whereas the gel liquid is found in the interior of the fibres and in pores on the surface thereof.

According to the Laplace equation [1], be pressure required to remove the gel liquid is greater than the pressure required to remove the capillary-bound liquid. It can be said therefore that the gel liquid is "firmly" bound to the material, whereas the capillary liquid is bound less firmly.

A comparison between so-called superabsorbents and pulp fibres shows that the difference in gel-liquid con is very eat when the liquid is comprised of water, 0.9% NaCl-solution, so-called synthetic urine or some other substance that swells superabsorbents.

The liquid porosymmetry method thus provides good possibilities of examining the ability of the material to retain firmly-bound liquid, and a distribution function which describes how the capillary, less firmly-bound, liquid is red in the material.

Figure 9:
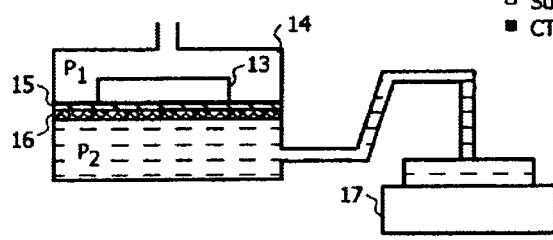
FIG. 9 shows an exemplary pore volume distribution apparatus.

FIG. 9 is a schematic illustration of the construction on of the PVD-apparatus.

Fibres from Example 1, spun in a bath containing 3 $AlCl_3$ $_6H_2O$/95 vol % ethanol and 5 vol % water, and fibres from Example 5 were characterized with the aid of the PVD-apparatus described above. Sample bodies were formed from the aforesaid fibres. So-called synthetic urine was used as test liquid and the materials were loaded with a pressure of 2.5 kPa during the measuring process.

The following materials were also tested for comparison purposes:

1. CTMP (Mölnlyeke)
2. Sulphate pulp (Korsnäs)
3. Superabsorbent powder, Sanwet® IM 2200D (Hoechst)

Result

Table 1 shows the values obtained with regard to gel liquid, capillary bound liquid and the total amount of liquid absorbed

TABLE 1

| Sample | Gel liquid g/g | Capillary liquid g/g | Total liquid g/g |
| --- | --- | --- | --- |
| CTMP | 1.37 | 8.78 | 10.75 |
| Sulphate pulp | 0.86 | 6.24 | 7.10 |
| Sanwet ® IM 2200D | 16.85 | 16.12 | 32.97 |
| CMC-fibres Example 1 | 19.90 | 10.00 | 29.90 |
| CMC-fibres Example 5 | 14.40 | 16.85 | 31.25 |

The ability of Sanwet® IM 200D and CMC-fibres to absorb gel liquid was found to be several times greater fin the ability of the pulp fibres. A comparison between the CMC-fibres from Example 1 and Example 5 shows that the covalently cross-linked fibres from Example 5 have a greater ability to take-up capillary-bound liquid.

Figure 10:
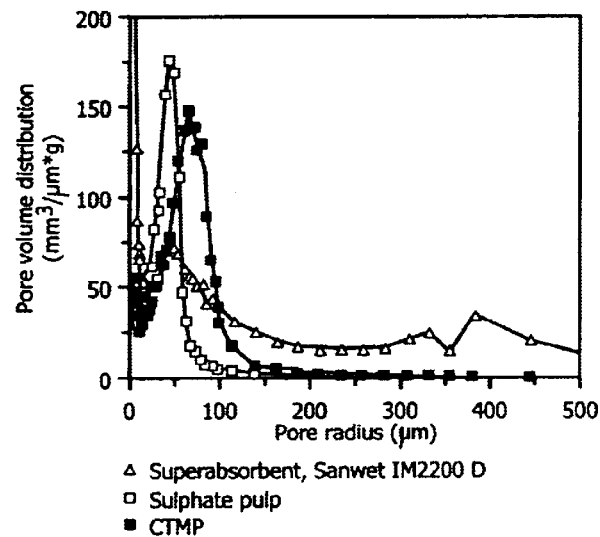
FIG. 10 is a graph showing an exemplary pore volume distribution.
Figure 11:
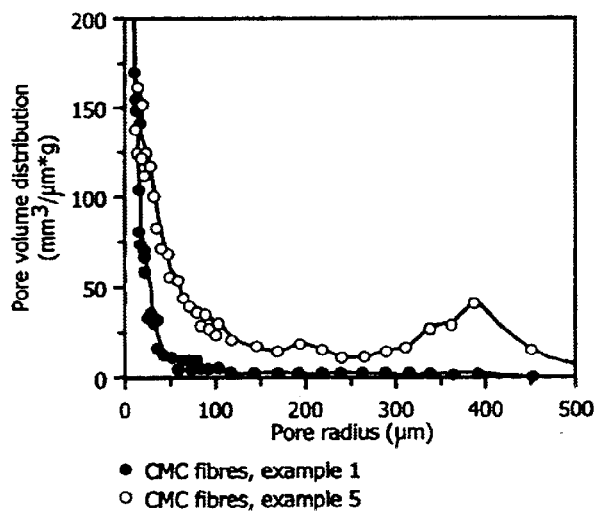
FIG. 11 is a graph showing an exemplary pore volume distribution.

FIGS. 10 and 11 illustrate the pore volume distribution of the materials tested. It will be seen from FIG. 11 that the fibre network comprised of covalently cross-linked CMC-fibres has larger pores than the fibres which are not covalently cross-inked. This should be advantageous from the aspect of flow resistance when liquid shall be transported between the fibres in an absorbent article. The pore structure of the commercial polyacrylate superabsorbent Sanwet® IM 2200D is equivalent to the pore structure of the covalently cross-linked CMC-fibre from Example 5.

EXAMPLE 7

Free Swelling Capacity of the Fibres

Free swelling capacity is defined as the swelling capacity of a material that is not subjected to pressure.

Figure 5:
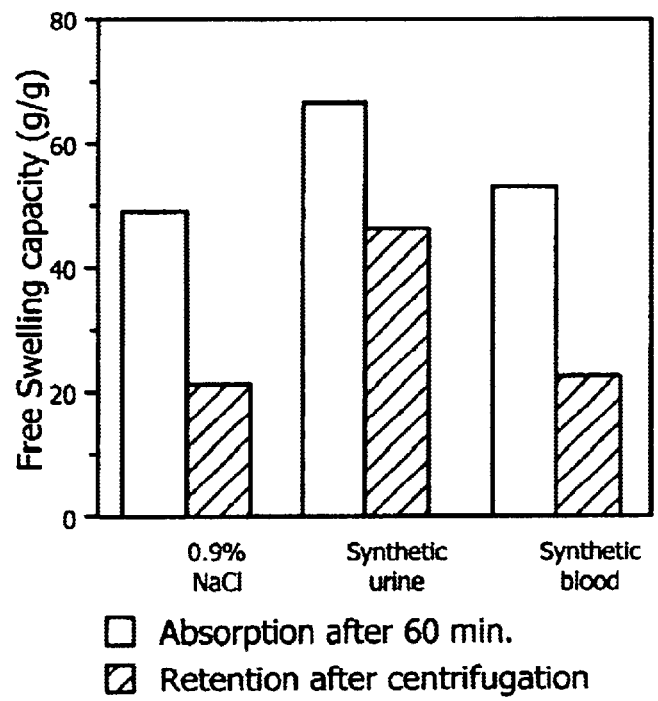
FIG. 5 is a graph showing the free swelling capacity of exemplary fibres.
Figure 6:
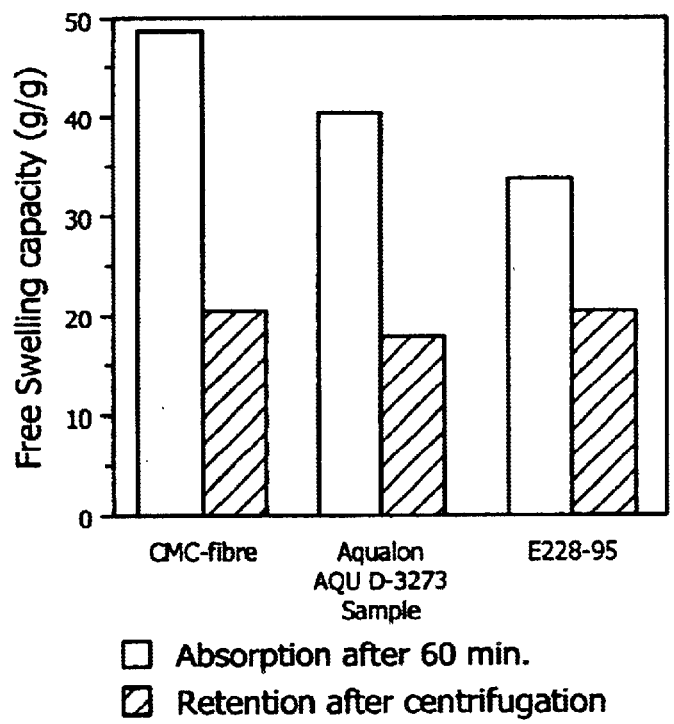
FIG. 6 is a graph showing the free swelling capacity of exemplary fibers and comparative materials.

FIG. 5 illustrates the free swelling capacity of CMC-fibres produced in accordance with Example 1 from Cekol 50000 and having an aluminium content of 7.7 g/kg. The liquids tested were 0.9% NaCl, synthetic wine and synthetic menstruation fluid. By synthetic urine and synthetic menstruation fluid is meat synthetically prepared liquids which were similar to their natural counterparts with regard to physical properties and chemical composition FIG. 6 illustrates a comparison with regard to free-swelling between CMC-fibres produced in accordance with Example 1 from Cekol 50000 and having an aluminum content of 7.7 g/kg, and two commercially available CMC-materials, Aqualon® ACU D-3273 (Hercules) and E228-95 (Hoechst). It will be seen from the Figure that CMC-fibres produced in accordance with Example 1 have a higher free-swelling capacity than the commercially available CMC-materials.

What is claimed is:

1. A method of producing polysaccharide fibers, comprising the steps of dissolving a polysaccharide in a solvent to form a solution, and spraying the solution into a bath which contains a water-miscible organic solvent and a cross-linker, wherein the solvent dissolving the polysaccharide is water, and wherein the cross-linker ionically cross-links the polysaccharide, wherein the polysaccharide fibers precipitate in the bath simultaneously with the ionic cross-linking of the polysaccharide.

2. A method of producing polysaccharide fibers according to claim 1, further comprising the steps of stretching, rolling-up, drying and cutting the polysaccharide fibers after the bath.

3. A method of producing polysaccharide fibers according to claim 1, wherein the organic solvent is an alcohol or a ketone.

4. A method of producing polysaccharide fibers according to claim 3, wherein the organic solvent is methanol, ethanol, isopropanol or acetone.

5. A method of producing polysaccharide fibers according to claim 1, wherein the cross-linker is a polyelectrolyte.

6. A method of producing polysaccharide fibers according to claim 5, wherein the cross-linker is polyvinylamine or hexadimethrinbromide.

7. A method of producing polysaccharide fibers according to claim 1, wherein the cross-linker is a salt where the cation in the salt is a metal ion.

8. A method of producing polysaccharide fibers according to claim 7, wherein the cation in the salt is divalent, trivalent or quadrivalent.

9. A method of producing polysaccharide fibers according to claim 8, wherein the cation in the salt is calcium, magnesium, iron, aluminum aluminum or zirconium.

10. A method of producing polysaccharide fibers according to claim 7, wherein the anion in the metal salt is chloride.

11. A method of producing polysaccharide fibers according to claim 1, wherein the polysaccharide is comprised of carboxymethyl cellulose, starch, gellan, pectin or alginate.

12. A method of producing polysaccharide fibers according to claim 1, further comprising the step of cross-linking the fiber covalently in a following stage.

13. A method of producing polysaccharide fibers according to claim 1, wherein the bath is acidic.

* * * * *